US00PP29788P2

(12) United States Plant Patent
Lane

(10) Patent No.: US PP29,788 P2
(45) Date of Patent: Nov. 6, 2018

(54) SWEET CHERRY TREE NAMED 'SPC342'

(50) Latin Name: *Prunus avium*
Varietal Denomination: SPC342

(71) Applicant: Her Majesty the Queen in Right of Canada as represented by the Minister of Agriculture and Agri-Food, Ottawa (CA)

(72) Inventor: William David Lane, Summerland (CA)

(73) Assignee: HER MAJESTY THE QUEEN IN RIGHT OF CANADA AS REPRESENTED BY THE MINISTER OF AGRICULTURE AND AGRI-FOOD, Ottawa, Ontario (CA)

( * ) Notice: Subject to any disclaimer, the term of this patent is extended or adjusted under 35 U.S.C. 154(b) by 0 days.

(21) Appl. No.: 15/530,324

(22) Filed: Dec. 22, 2016

Related U.S. Application Data

(60) Provisional application No. 62/387,957, filed on Jan. 11, 2016.

(51) Int. Cl.
*A01H 5/08* (2018.01)

(52) U.S. Cl.
USPC ..... Plt./181

(58) Field of Classification Search
USPC ..... Plt./181, 180
CPC .... A01H 5/085; A01H 5/0216; A01H 5/0827; A01H 5/08; A01H 6/7445
See application file for complete search history.

(56) References Cited

PUBLICATIONS

University of Minnesota Extension 2018, retrieved on Jan. 24, 2018, retrieved from the Internet at https://www.extension.umn.edu/garden/yard-garden/fruit/integrated-pest-management-for-home-stone-fruit-growers/cherry-leaf-spot/, 2 pp. (Year: 2018).*
Upov Pluto Plant Variety Database Jan. 20, 2018, retrieved on Jan. 24, 2018, retrieved from the Internet at https://www3.wipo.int/pluto/user/en/index.jsp, one page. (Year: 2018).*

* cited by examiner

*Primary Examiner* — June Hwu
(74) *Attorney, Agent, or Firm* — Penny J. Aguirre

(57) ABSTRACT

A new cultivar of sweet cherry tree, 'SPC342', that is characterized by its very high fruit stem pull force, its large fruit with an attractive appearance, its flowers that are not self-fertile, its distinctive maroon spots on its leaves, and its good fruit storage capacity in MAP (modified atmosphere packaging).

2 Drawing Sheets

Botanical classification: *Prunus avium.*
Variety denomination: 'SPC342'.

BACKGROUND OF THE INVENTION

The present invention relates to a new and distinct cultivar of *Prunus avium* and will be referred to hereafter by its cultivar name, 'SPC342'. 'SPC342' is a new cultivar of sweet cherry tree grown for fruit production.

The new cultivar of *Prunus* arose from a breeding program conducted by the Inventor at a research center in Summerland, BC, Canada with the goal of developing new cultivars of cherry tree that would have improvements to the fruit appearance, fruit taste, fruit flesh texture, tree quality, productivity and precocity.

'SPC342' originated as a seedling that arose from seed planted from open pollination of *Prunus avium* 'Lapins' (not patented). 'SPC342' was selected as a single unique tree in 2000 from amongst the resulting seedlings.

Asexual propagation of the new cultivar was first accomplished by chip budding and grafted onto *Prunus avium* rootstock by the Inventor in Summerland, BC, Canada in 2003. Asexual propagation by chip budding and grafting has determined that the characteristics of the new cultivar are stable and are reproduced true to type in successive generations.

SUMMARY OF THE INVENTION

The following traits have been repeatedly observed and represent the characteristics of the new cultivar. These attributes in combination distinguish 'SPC342' as a unique cultivar of cherry tree.

1. 'SPC342' exhibits a very high fruit stem pull force.
2. 'SPC342' exhibits large fruit with an attractive appearance.
3. 'SPC342' exhibits flowers that are not self-fertile.
4. 'SPC342' exhibits distinctive maroon spots on its leaves.
5. 'SPC342' exhibits good fruit storage capacity in MAP (modified atmosphere packaging).

'Lapins', the female parent of 'SPC342', differs from 'SPC342' in having a later fruit maturity and in having smaller sized fruit. 'SPC342' can be most closely compared to the sweet cherry cultivars *Prunus avium* 'Bing' (not patented) and *Prunus avium* 'Sumnue' (not patented). 'Bing' is similar to 'SPC342' in fruit harvest timing. 'Bing' differs from 'SPC342' in having fruit that is smaller in size, in having a lower fruit stem pull force and in having different alleles. 'Sumnue' is similar to 'SPC342' in eating quality and in having cherries that are dark red in color. 'Sumnue' differs from 'SPC342' in having a slightly earlier fruit harvest date, in having fruit that is smaller in size, in having a lower fruit stem pull force and in having different alleles.

BRIEF DESCRIPTION OF THE DRAWINGS

The accompanying colored photographs illustrate the overall appearance and distinct characteristics of the sweet cherry, 'SPC342'. The photographs were taken of a seven year-old plant of 'SPC342' as grown outdoors in a trial plot in Summerland, BC, Canada.

Figure 1:
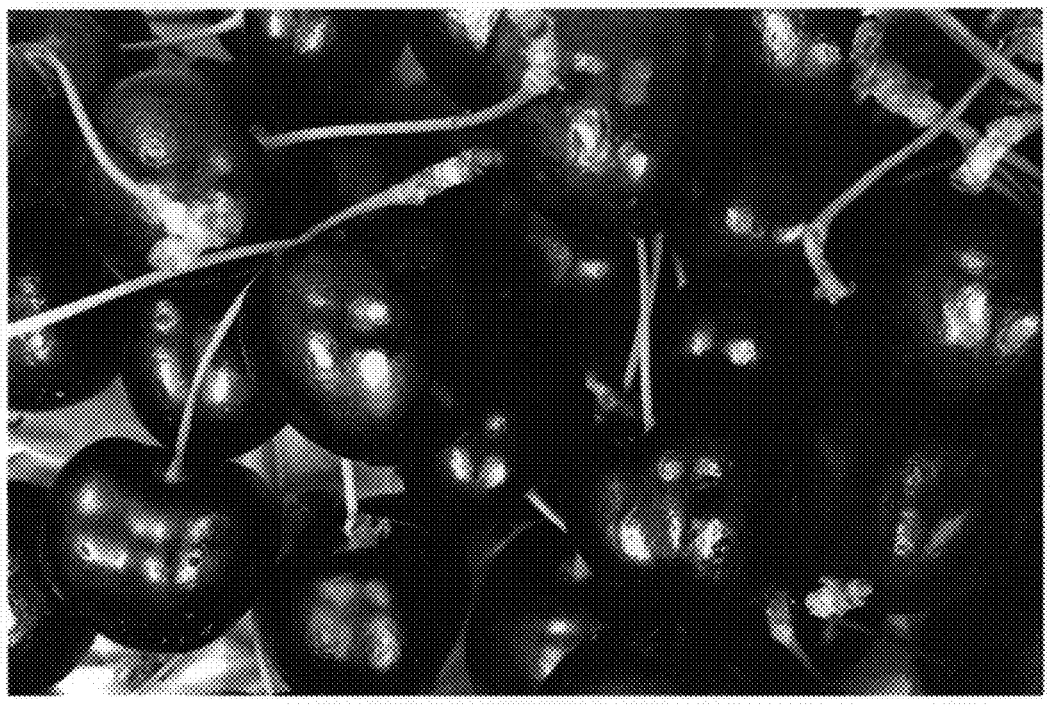
FIG. 1 provides a side view of multiple fruits of 'SPC342'.
Figure 2:
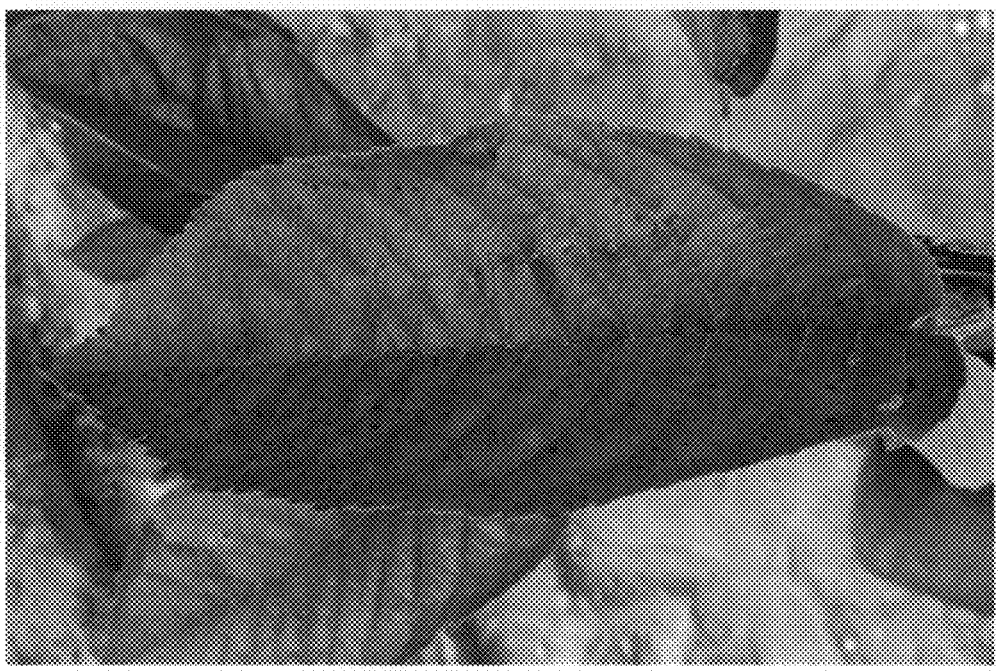
FIG. 2 provides a close-up view of a leaf of 'SPC342'.

The colors in the photographs are as close as possible with the digital photography and printing techniques utilized and the color codes in the detailed botanical description accurately describe the new cherry tree.

DETAILED BOTANICAL DESCRIPTION

The following is a detailed description of seven year-old trees as grown outdoors in a trial plot in Summerland, B.C., Canada. The phenotype of the new cultivar may vary with variations in environmental, climatic, and cultural conditions, as it has not been tested under all possible environmental conditions. The color determination is in accordance with The 2007 R.H.S. Colour Chart of The Royal Horticultural Society, London, England, except where general color terms of ordinary dictionary significance are used.

General description:

*Blooming period*.—Mid-season.
*Plant type*.—Deciduous fruit bearing tree.
*Plant habit*.—Upright and spreading.
*Height and spread*.—Reaches an average of 3.9 m in height and about 2.4 m in width.
*Cold hardiness*.—At least to U.S.D.A. Zone 6A.
*Diseases and pests*.—No susceptibility or resistance to diseases or pests has been observed.
*Root description*.—Fibrous, freely branched, color Brown Group 200B.
*Propagation*.—Chip budding and grafting.
*Root development*.—1 year to produce a young plant from budding.
*Growth rate*.—Moderately vigorous.

Trunk description:

*Size of trunk*.—23 cm in diameter measured 30 cm above soil level.
*Bark color*.—Greyed-Purple 187A with Horizontal stripes of Greyed-Green 198B.
*Bark texture*.—Stripes are smooth.

Description of dormant shoots (1 year-old):

*Branching*.—Moderate.
*Pubescence*.—Absent.
*Shoot size*.—An average of 75 cm in length and 7.2 mm in width.
*Anthocyanin presence*.—Absent.
*Thickness of shoot at center of middle internode*.—Moderate to thick; an average of 7.2 mm.
*Bark color*.—Greyed-Orange 166C.
*Bark surface*.—Smooth with raised lenticels.
*Shoot angle*.—Semi-erect.
*Lenticels*.—Numerous, 164D in color, round, an average of 1.3 mm in diameter, an average of 4 per square cm.
*Branch internode length*.—Moderately long; average of 4.1 cm.
*Vegetative buds*.—Moderately large in size; 7.4 mm in length and 3.3 mm in width, conical in shape, held slightly out from shoot, moderate to high support.

Description of growing shoots:

*Color of growing tip of shoot*.—Greyed-Purple 185A.
*Pubescence of shoots tip*.—Absent.
*Anthocyanin presence*.—Absent.
*Surface*.—Smooth.

Foliage description:

*Leaf shape*.—Broad ovate to elliptic.
*Leaf division*.—Simple.
*Leaf base*.—Rounded.
*Leaf apex*.—Acute and acuminate to cuspidate at very tip.
*Leaf fragrance*.—None.
*Leaf burst*.—Typically 1 week of May.
*Leaf venation*.—Pinnate, not prominent, same as leaf color with the midrib on upper surface Yellow-Green Group 144D and lower surface Yellow-Green Group 144D.
*Leaf margins*.—Serrate.
*Leaf arrangement*.—Alternate.
*Leaf aspect*.—Concave and held horizontal to slightly downward in relation to shoot.
*Leaf attachment*.—Petiolate.
*Leaf surface*.—Slightly pubescent on lower surface and weak to upper surface moderately glossy on upper surface.
*Leaf size*.—Mature leaves average 13.7 cm in length and 7.0 cm in width.
*Leaf internodes*.—An average of 4.3 cm.
*Leaf color*.—Newly expanded leaves upper surface; Yellow-Green Group 144B, newly expanded leaves lower surface; Greyed-Purple Group 185A, leaves are fringed with Greyed-Purple Group 185A, mature leaves upper surface; Green Group 137A with small round to oval spots of 183A, mature leaves lower surface; Green Group 138C.
*Petioles*.—Average of 3.6 cm in length and 2.0 mm in width, Yellow-Green Group 144D in color with anthocyanin Greyed-Purple Group 185A, typically 3 nectaries that are kidney-shaped and Greyed-Purple Group 185A in color, glabrous surface.

Inflorescence description:

*Blooming period*.—Blooms on average in the middle of the cherry bloom period in B.C., Canada.
*Inflorescence type*.—Clusters of single flowers.
*Lastingness of inflorescence*.—+6 days.
*Flower fragrance*.—Minimal.
*Flower quantity*.—Medium density.
*Flower type*.—Rotate corolla above an elongated calyx with stamens and pistil extended.
*Flower size*.—Large; an average of 3.6 cm in diameter.
*Calyx*.—Comprised of sepals fused into an ovoid base with un-fused portions spreading at apex.
*Sepals*.—5, yellow-green 144B in color, glabrous on both surfaces, un-fused portions about 4.0 mm in width and 5.8 mm length, entire glandular margin, attenuate apex, fused base.
*Petals*.—5, obovate in shape, un-fused, overlapping, entire margin, oblique base, retuse apex, about 1.5 cm in length and 1.3 cm in width, White 155D in color (upper and lower surface), smooth on upper and lower surface.

*Pedicels*.—Average of 28.4 mm in length, 1.1 mm in width, Yellow-Green Group 144C in color, glabrous surface. Flowers lightly compacted with whorled arrangement.

Reproductive organs:

*Gynoecium*.—1 pistil about 1.7 cm in length and <1 mm in width extending beyond perianth, style is Yellow-Green Group 145C in color and about 13.1 mm in length, stigma is about <1 mm in diameter and Yellow-Green Goup 145B in color, ovary is superior, glabrous and Yellow-Green Group 144A in color.

*Androecium*.—Average of 40 stamens, base adnate to calyx, filaments are white group 155D in color, about 13.1 mm in length and <1 mm in width, anthers are Greyed-Orange Group 163D in color, dorsifixed, about 2 mm in length and 1 mm in width, pollen is abundant in quantity and about Greyed-Orange Group 163B in color.

*Fertility*.—Self-fertile.

Fruit description:

*Fruit type*.—Drupe.

*Fruit shape*.—Kidney-heart shaped (lateral view is flattened), flat apex.

*Fruit apex*.—Flat with low susceptibility to rain induced cracking.

*Fruit size*.—Very large; 2.8 cm in length and 3.1 cm in width.

*Fruit firmness*.—Firm.

*Fruit set*.—Medium.

*Fruit stalk*.—Long; average of 5.2 cm in length and 1.4 mm wide, surface color Yellow-Green Group 144D.

*Fruit bearing*.—Medium.

*Number of fruit per cluster*.—1-3.

*Skin color*.—A blend of Black Group 202A when ripe with a moderate quantity of small lenticels 18B in color.

*Skin suture*.—Moderate prominence.

*Harvest date*.—Mid harvest season; July 10 in Summerland, BC, Canada.

*Skin surface*.—Glossy.

*Flesh and juice color*.—Red Group 53A.

*Flesh texture*.—Fleshy, moderately juicy.

*Flavor*.—Medium degree of sweetness.

*Weight*.—An average of 14.4 g/berry.

*Fruit yield* (*productivity*).—30 lbs./tree, yield between Bing and Lapins.

*Brix*.—21.4%.

*Acidity*.—Low to medium.

*Fruit storage*.—Minimum of 5 weeks in MAP bags (modified atmosphere packaging) under common storage conditions with an average temperature of 34° F.

*Market use*.—Fresh fruit market.

*Seeds*.—1 stone per berry, Greyed-Orange Group 165D in color, large in size; average of 12.1 mm in length and 10.5 mm in width, 8.3 mm in thickness semi adherent to flesh, shape; lateral view is symmetrical and spherical to elongate, front view is elliptic, basal view is round, keel is very strongly developed.

It is claimed:

1. A new and distinct cultivar of sweet cherry tree named 'SPC342' as herein illustrated and described.

* * * * *